(12) United States Patent
Hale et al.

(10) Patent No.: US 9,328,044 B2
(45) Date of Patent: May 3, 2016

(54) PROCESSES FOR MAXIMIZING ETHANOL FORMATION IN THE HYDROGENATION OF ACETIC ACID

(71) Applicant: Celanese International Corporation, Irving, TX (US)

(72) Inventors: Trinity Horton Hale, Houston, TX (US); Radmila Wollrab, Pasadena, TX (US); Victor J. Johnston, Houston, TX (US); Tianshu Pan, Houston, TX (US); R. Jay Warner, Houston, TX (US); Heiko Weiner, Pasadena, TX (US); Nathan Bower, Houston, TX (US); Josefina T. Chapman, Houston, TX (US); Gerald Grusendorf, Rosharon, TX (US)

(73) Assignee: CELANESE INTERNATIONAL CORPORATION, Irving, TX (US)

(*) Notice: Subject to any disclaimer, the term of this patent is extended or adjusted under 35 U.S.C. 154(b) by 137 days.

(21) Appl. No.: 14/027,740

(22) Filed: Sep. 16, 2013

(65) Prior Publication Data
US 2014/0046100 A1    Feb. 13, 2014

Related U.S. Application Data

(62) Division of application No. 12/940,595, filed on Nov. 5, 2010, now Pat. No. 8,552,224.

(60) Provisional application No. 61/332,702, filed on May 7, 2010.

(51) Int. Cl.
C07C 29/147 (2006.01)
C07C 29/149 (2006.01)
C07C 29/80 (2006.01)

(52) U.S. Cl.
CPC .............. *C07C 29/147* (2013.01); *C07C 29/149* (2013.01); *C07C 29/80* (2013.01)

(58) Field of Classification Search
CPC combination set(s) only.
See application file for complete search history.

(56) References Cited

U.S. PATENT DOCUMENTS 2,607,807 A    8/1952  Ford
2,649,407 A    8/1953  Harrison et al.
(Continued)

FOREIGN PATENT DOCUMENTS

CN    102229520    11/2011
EP      0104197     4/1984
(Continued)

OTHER PUBLICATIONS

Office Action for corresponding Chinese Appl. No. 201180001921.4 mailed Aug. 2, 2013.
(Continued)

*Primary Examiner* — Karl J Puttlitz
(74) *Attorney, Agent, or Firm* — Kilpatrick Townsend & Stockton LLP

(57) ABSTRACT

In one embodiment, the invention is to a process for purifying a crude ethanol product. The process comprises the step of hydrogenating acetic acid in a reactor in the presence of a catalyst to form the crude ethanol product. The process further comprises the step of separating at least a portion of the crude ethanol product in a purification zone. The purification zone preferably comprises a first column, which yields a first distillate comprising ethanol, water and ethyl acetate, and a first residue comprising acetic acid. The at least a portion of the crude ethanol product has a residence time from the reactor to the purification zone from 5 minutes to 5 days.

9 Claims, 6 Drawing Sheets

(56) References Cited

U.S. PATENT DOCUMENTS

| | | | |
|---|---|---|---|
| 2,882,244 A | 4/1959 | Milton | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,990,952 A | 11/1976 | Katzen et al. | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,379,028 A | 4/1983 | Berg et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,520,213 A | 5/1985 | Victor | |
| 4,541,897 A | 9/1985 | Sommer et al. | |
| 4,626,321 A | 12/1986 | Grethlein et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,842,693 A | 6/1989 | Wheldon | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,061,671 A | 10/1991 | Kitson et al. | |
| 5,124,004 A | 6/1992 | Grethlein et al. | |
| 5,144,068 A | 9/1992 | Smith et al. | |
| 5,149,680 A | 9/1992 | Kitson et al. | |
| 5,185,481 A | 2/1993 | Muto et al. | |
| 5,233,099 A | 8/1993 | Tabata et al. | |
| 5,237,108 A | 8/1993 | Marraccini et al. | |
| 5,250,271 A | 10/1993 | Horizoe et al. | |
| 5,348,625 A | 9/1994 | Berg | |
| 5,415,741 A | 5/1995 | Berg | |
| 5,437,770 A | 8/1995 | Berg | |
| 5,445,716 A | 8/1995 | Berg | |
| 5,449,440 A | 9/1995 | Rescalli et al. | |
| RE35,377 E | 11/1996 | Steinberg et al. | |
| 5,599,976 A | 2/1997 | Scates et al. | |
| 5,821,111 A | 10/1998 | Gaddy et al. | |
| 6,121,498 A | 9/2000 | Tustin et al. | |
| 6,143,930 A | 11/2000 | Singh et al. | |
| 6,232,352 B1 | 5/2001 | Vidalin et al. | |
| 6,294,703 B1 | 9/2001 | Hara et al. | |
| 6,375,807 B1 | 4/2002 | Nieuwoudt et al. | |
| 6,509,180 B1 | 1/2003 | Verser et al. | |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,723,886 B2 | 4/2004 | Allison et al. | |
| 6,809,217 B1 | 10/2004 | Colley et al. | |
| 6,906,228 B2 | 6/2005 | Fischer et al. | |
| 6,927,048 B2 | 8/2005 | Verser et al. | |
| 7,005,541 B2 | 2/2006 | Cheung et al. | |
| 7,115,772 B2 | 10/2006 | Picard et al. | |
| 7,199,212 B2 | 4/2007 | Nakajima et al. | |
| 7,208,624 B2 | 4/2007 | Scates et al. | |
| 7,297,236 B1 | 11/2007 | Vander Griend et al. | |
| 7,351,559 B2 | 4/2008 | Verser et al. | |
| 7,507,562 B2 | 3/2009 | Verser et al. | |
| 7,553,397 B1 | 6/2009 | Colley et al. | |
| 7,572,353 B1 | 8/2009 | Vander Griend | |
| 7,594,981 B2 | 9/2009 | Ikeda | |
| 7,608,744 B1 * | 10/2009 | Johnston et al. | 568/885 |
| 7,744,727 B2 | 6/2010 | Blum et al. | |
| 7,863,489 B2 | 1/2011 | Johnston et al. | |
| 7,947,746 B2 | 5/2011 | Daniel et al. | |
| 8,071,821 B2 | 12/2011 | Johnston et al. | |
| 8,378,153 B2 | 2/2013 | Daniel et al. | |
| 8,425,733 B2 | 4/2013 | Halvorsen et al. | |
| 8,502,001 B2 | 8/2013 | Daniel et al. | |
| 8,524,954 B2 | 9/2013 | Ditzel et al. | |
| 2006/0019360 A1 | 1/2006 | Verser et al. | |
| 2006/0070867 A1 | 4/2006 | Ikeda | |
| 2007/0270511 A1 | 11/2007 | Melnichuk et al. | |
| 2008/0135396 A1 | 6/2008 | Blum | |
| 2009/0014313 A1 | 1/2009 | Lee et al. | |
| 2009/0023192 A1 | 1/2009 | Verser et al. | |
| 2009/0081749 A1 | 3/2009 | Verser et al. | |
| 2009/0166172 A1 | 7/2009 | Casey et al. | |
| 2009/0221725 A1 | 9/2009 | Chorney et al. | |
| 2009/0318573 A1 | 12/2009 | Stites et al. | |
| 2010/0029980 A1 | 2/2010 | Johnston et al. | |
| 2010/0029995 A1 | 2/2010 | Johnston et al. | |
| 2010/0121114 A1 | 5/2010 | Johnston et al. | |
| 2010/0197485 A1 | 8/2010 | Johnston et al. | |
| 2011/0098501 A1 | 4/2011 | Johnston et al. | |
| 2011/0190547 A1 | 8/2011 | Jevtic et al. | |
| 2011/0190548 A1 | 8/2011 | Jevtic et al. | |
| 2011/0263911 A1 | 10/2011 | Johnston et al. | |
| 2013/0217925 A1 | 8/2013 | Chornet et al. | |

FOREIGN PATENT DOCUMENTS

| | | |
|---|---|---|
| EP | 0167300 | 1/1986 |
| EP | 0456647 | 11/1991 |
| EP | 2060553 | 5/2009 |
| EP | 2072487 | 6/2009 |
| EP | 2072488 | 6/2009 |
| EP | 2072492 | 6/2009 |
| WO | WO 83/03409 | 10/1983 |
| WO | 2007003897 | * 1/2007 |
| WO | WO 2008/135192 | 11/2008 |
| WO | WO 2009/009322 | 1/2009 |
| WO | WO 2009/009323 | 1/2009 |
| WO | WO 2011/053365 | 5/2011 |

OTHER PUBLICATIONS

International Search Report and Written Opinion for PCT/US2011/023273 mailed Sep. 8, 2011.

Santori et al.(2000). Hydrogenation of carbonylic compounds on Pt/SiO2 catalysts modified with SnBu4, Studies in Surface Science and Catalysis, 130, 2063-2068.

ZeaChem, Inc., Technology Overview, Lakewood, Colorado www.zeachem.com, 2008.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Zheng, et al., (2007). Preparation and catalytic properties of a bimetallic Sn—Pt complex in the supercages of NaY zeolite by use of surface organometallic chemistry, Applied Organometallic Chemistry, 21(10), 836-840.

(56) References Cited

OTHER PUBLICATIONS

Yu Huang, et al., "Low-Energy Distillation-Membrane separation Process", Industrial & Engineering Chemistry Research, Am. Chem. Soc., vol. 49, No. 8, Jan. 1, 2010, pp. 3760-3768.

Zhu, Y. et al. (Apr. 2009). "Techno-economic Analysis for the Thermochemical Conversion of Lignocellulosic Biomass to Ethanol via Acetic Acid Synthesis," PNNL-18483, *Pacific Northwest National Laboratory*, Richland, WA.

Taiwan Office Action mailed on Jan. 19, 2015, for TW Patent Application No. 100103896, with English translation, 7 pages.

Australian Office Action mailed on Jun. 17, 2014, for AU Patent Application No. 2011213126, 4 pages.

Chinese Office Action for Chinese Appl. No. 201180001921.4 dated Feb. 26, 2014.

Office Action for corresponding Chinese Appl. No. 201180001921.4 dated Jul. 3, 2014.

Chinese Office Action mailed on May 29, 2015 for CN Patent Application No. 201180001921.4, 21 pages.

\* cited by examiner

PROCESSES FOR MAXIMIZING ETHANOL FORMATION IN THE HYDROGENATION OF ACETIC ACID

CROSS REFERENCE TO RELATED APPLICATIONS

This application is a divisional application of U.S. application Ser. No. 12/940,595, filed Nov. 5, 2010, which claims priority to U.S. Provisional Application No. 61/332,702, filed on May 7, 2010, the disclosure of which is hereby incorporated by reference.

FIELD OF THE INVENTION

The present invention relates generally to processes for producing ethanol and, in particular, to processes for maximizing ethanol formation in the hydrogenation of acetic acid by reducing ethyl acetate formation.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol for fuels or consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are often formed with ethanol or are formed in side reactions. For example, during hydrogenation and/or in subsequent side reactions, esters are produced that together with ethanol and/or water may form azeotropes, which are difficult to separate. These impurities may limit the production of ethanol and may require expensive and complex purification trains to separate the impurities from the ethanol. In addition, when conversion is incomplete, unreacted acid remains in the crude ethanol product. This residual acetic acid may, with time, promote additional detrimental side reactions. Accordingly, the residual acetic acid must be removed from the crude ethanol product to yield purified ethanol.

Therefore, the need remains for improving the recovery of ethanol from a crude product obtained by reducing alkanoic acids, such as acetic acid, and/or other carbonyl group-containing compounds. In addition, the need exists for processes that reduce or inhibit the formation of impurities via detrimental side reactions.

SUMMARY OF THE INVENTION

In a first embodiment, the present invention is directed to a process for purifying a crude ethanol product, comprising hydrogenating acetic acid in a reactor in the presence of a catalyst to form the crude ethanol product; and separating at least a portion of the crude ethanol product in a downstream purification zone into one or more derivative streams. Preferably, the purification zone comprises a first column, which yields a first distillate comprising ethanol, water and ethyl acetate, and a first residue comprising acetic acid. In a preferred embodiment, at least a portion of the crude ethanol product has a residence time from the reactor to the first column from 5 minutes to 5 days. In some embodiments, a holding tank is configured between the reactor and the first column and the crude ethanol product has a residence time from the reactor to the first column ranging from 1 hour to 5 days, e.g., from 1 day to 3 days. In other embodiments, where a holding tank is not employed, the crude ethanol product has a residence time from the reactor to the purification zone ranging from 1 second to 1 hour, e.g., from 5 minutes to 30 minutes or from 5 minutes to 15 minutes.

In a second embodiment, the inventive processes comprise the step of hydrogenating acetic acid in a reactor in the presence of a catalyst to form the crude ethanol product; separating the crude ethanol product in a flasher into a vapor stream and a liquid stream; directing at least a portion of the liquid stream to a downstream purification zone; and separating at least a portion of the liquid stream in the purification zone into at least one derivative stream. Preferably, the purification zone comprises a first column, which yields a first distillate comprising ethanol, water and ethyl acetate, and a first residue comprising acetic acid. The at least a portion of the liquid stream has a residence time from the flasher to the purification zone from 5 minutes to 5 days.

In a third embodiment, the inventive processes comprise hydrogenating acetic acid in a reactor in the presence of a catalyst to form the crude ethanol product; and separating the crude ethanol product in a flasher into a vapor stream and a liquid stream, cooling at least a portion of the liquid stream to a temperature from 0 to 40° C.; directing at least a portion of the liquid stream to a purification zone; and separating at least a portion of the liquid stream in the purification zone into at least one derivative stream.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
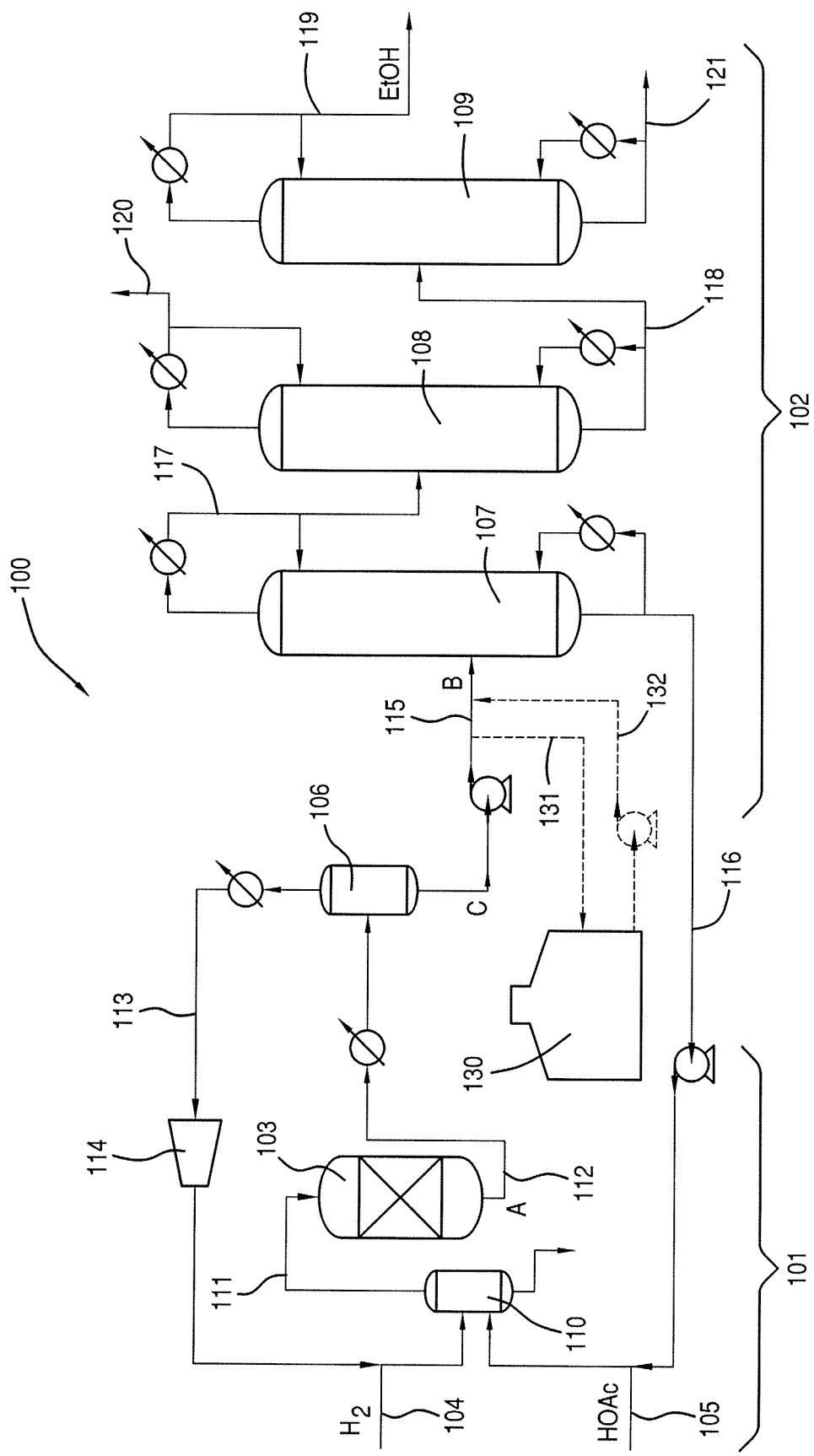
FIG. 1 is a schematic diagram of a hydrogenation system having a holding tank in accordance with one embodiment of the present invention.

The present invention relates to processes for recovering ethanol from a crude ethanol product. In particular, the present invention relates to processes for recovering and/or purifying ethanol from a crude ethanol product, which preferably is formed in a process for hydrogenating acetic acid in the presence of a catalyst. Once formed, the crude ethanol product is directed to a purification zone for separating the various components contained therein, e.g., ethanol, water, and residual acetic acid.

In particular, the processes of the present invention relate to suppressing and/or reducing the formation of ethyl acetate in the crude ethanol product prior to residual acetic acid removal in the purification zone. A non-catalyzed reaction occurs in the crude ethanol product driving the crude ethanol product to an equilibrium between ethanol/acetic acid and ethyl acetate/water as shown below:

$$EtOH + HOAc \rightleftharpoons EtOAc + H_2O$$

In product mixtures comprising more ethanol and acetic acid than ethyl acetate and water, such as the crude ethanol product, this equilibrium reaction will undesirably lead to the formation of additional ethyl acetate and water at the expense of the desired ethanol product. This effect decreases ethanol productivity and increases waste. The reaction rate of this equilibrium reaction increases with temperature.

In preferred embodiments, the crude ethanol product, once formed, is directed to a purification zone for separation of the components contained in the crude ethanol product. The purification zone yields at least one, e.g., at least two or at least three, derivative stream(s). The purification zone separates the residual acetic acid from the product ethanol. Preferably, the purification zone comprises a first column, which yields a first distillate comprising ethanol, water and ethyl acetate, and a first residue comprising acetic acid. In such cases, the first distillate and the first residue may be considered derivative streams.

In another embodiment, the separation of the residual acetic acid from the product ethanol is achieved via other purification unit(s). In many chemical processes, for example, distillation columns consume a significant amount of energy. Thus, in embodiments where reduced energy consumption is desired, one or more membrane separation units are employed to purify the crude ethanol product. Preferably, the membrane separation unit comprises a pervaporation membrane. The crude ethanol product and/or the one or more derivative streams may be passed through the membrane separation unit(s). In one embodiment, the membrane separation unit is used in conjunction with the distillation column(s). In some embodiments, the membranes may replace the necessity for one or more, e.g., two or more, distillation columns. The use of one or more membranes provides a low energy alternative to distillation columns. In addition, the use of membrane separation unit(s) may advantageously provide the ability to "break" azeotropes without the use of entrainers. For applications in which the crude ethanol product comprises ethanol and water, the one or more membranes may break the ethanol-water azeotrope. The ethanol-water azeotrope limits the recoverable ethanol in distillation columns to an ethanol product comprising about 92-96 wt. % of ethanol. Membranes are preferably suited to providing an ethanol product, such as an anhydrous ethanol product, with higher amounts of ethanol, e.g., at least 96 wt. % or greater or at least 99 wt. % or greater.

Typically, substantially all of the residual acetic acid is first separated and/or removed from the crude ethanol product in the purification zone. Once the residual acetic acid is removed, the formation of ethyl acetate according to the above equilibrium reaction is effectively arrested. According to preferred embodiments of the invention, the residence time between the formation of the crude ethanol product and the separation and/or removal of the residual acetic acid in the purification zone is kept sufficiently low so as to effectively reduce ethyl acetate formation. In some embodiments, since the reaction rate of the equilibrium reaction increases with temperature, the process additionally or alternatively involves maintaining the crude ethanol product at temperatures sufficient to slow or inhibit the formation of ethyl acetate until the residual acetic acid can be effectively removed therefrom.

Thus, in one embodiment, the amount of ethyl acetate formed in the crude ethanol product may be minimized by providing a low residence time between formation of the crude ethanol product and the substantial removal of residual acetic acid therefrom, e.g., in the purification zone. It should be noted that the specific separation scheme employed in the purification zone may vary widely. As a result, the step of substantially removing the residual acetic acid may be the first step or a subsequent step in the purification system. For some embodiments of the present invention, the relevant time period is the time between formation of the crude ethanol product and the time that the crude ethanol product is introduced into a separation unit of the purification zone to remove residual acetic acid therefrom. This time period may be critical because removal of the residual acetic acid may be primarily responsible for arresting the ethanol/ethyl acetate equilibrium reaction. The separation unit, e.g., purification column, that is primarily responsible for removing residual acetic acid is also referred to herein as the acid removal unit.

Referring to FIG. 1, in one embodiment, the residence time is the period of time between the time that the crude ethanol product exits reactor 103 (point A) and the time that the crude ethanol product enters the acid removal unit 107 (point B). In this embodiment, the crude ethanol product preferably has a residence time of less than 5 days, e.g., less than 3 days, less than 1 hour, less than 30 minutes, less than 15 minutes, or less than 5 minutes. In terms of ranges, the residence time optionally is from 5 minutes to 5 days, e.g., from 5 minutes to 3 days, or from 5 minutes and 1 hour.

In some embodiments, as shown in FIG. 1, the crude ethanol product derived from reactor 103 is flashed in a flasher 106 to remove hydrogen and light hydrocarbons therefrom prior to introduction to the acid removal unit 107. In this aspect, the stream exiting the flasher 106 also may be referred to as a crude ethanol product stream. Thus, in some aspects, the invention is characterized in terms of the residence time of the crude ethanol product between the time that it exists the flasher (point C) and the time that it is introduced into acid removal unit (point B). In this embodiment, the crude ethanol product may have a residence time of less than 5 days, e.g., less than 3 days, less than 1 hour, less than 30 minutes, less than 15 minutes, or less than 5 minutes.

By minimizing the specified residence time, the amount of additional ethyl acetate formed prior to introduction into the purification zone 102, and more specifically into the acid removal unit 107, also can be effectively minimized. In some embodiments, the reaction zone 101 is closely coupled with the purification zone 102.

In other embodiments, a holding tank 130 is provided between these two zones, for example, to allow a portion the crude ethanol product to be transported to a separate location for purification. All or a portion of the crude ethanol product may be held in the holding tank prior to introduction into the purification zone 102, e.g., into the acid removal unit. The residence time of the crude ethanol product between points A and C, when held in one or more holding tanks, is preferably less than the residence time between points C and B, and may be from 5 minutes to 5 days, e.g., from 5 minutes to 3 days, or from 5 minutes and 1 hour. Exemplary residence times between points C and B, when held in a holding tank, is from 5 minutes to 5 days, e.g., from 5 minutes to 3 days, or from 5 minutes and 1 hour. In various optional embodiments, the one or more holding tanks may be provided between points A and C, between points C and B, or both between points A and C and between points C and B.

In some embodiments where a holding tank is not employed, the crude ethanol product may have a shorter residence time, as measured from point A to point B or from point C to point B, than in cases where a holding tank is employed. For example, in some embodiments where a holding tank is not employed, the crude acetic acid product may have a residence time less than 1 hour, e.g., less than 30 minutes, less than 15 minutes, or less than 5 minutes. In terms of ranges, the residence time, as measured from point A to point B or from point C to point B, may range from 1 second to 1 hour, e.g., from 5 minutes to 30 minutes or from 5 minutes to 15 minutes.

In other embodiments where a holding tank is used, the crude ethanol product, may have a longer residence time, as measured from point A to point B or from point C to point B, than in cases where a holding tank is not used. For example, in some embodiments where a holding tank is employed, the crude acetic acid product may have a residence time less than 5 days, e.g., less than 3 days, or less than 1 day. In terms of ranges, the residence time, as measured from point A to point B or from point C to point B, may range from 1 hour to 5 days, e.g., from 1 day to 3 days. In terms of lower limits, the residence time in these cases may be at least 1 hour, e.g., at least 1 day. In comparing residence times with and without a holding tank, the residence time when using a holding tank may be at least 10% longer than the residence time when not using a holding tank, e.g., at least 25%, at least 50%, at least 100%, or at least 200%.

In another embodiment, as indicated above, additional formation of ethyl acetate in the crude ethanol product may additionally or alternatively be controlled by maintaining the crude ethanol product at a temperature less than 40° C., e.g., less than 30° C. or less than 20° C. In terms of ranges, the crude ethanol product may be maintained at a temperature from 0° C. to 40° C., e.g., from 0° C. to 30° C. or from 0° C. to 20° C. The temperature preferably is maintained at these temperatures between the flasher and the purification zone, e.g., the acid removal unit, e.g., between points C and B in FIG. 1. One or more cooling devices or heat exchangers may be used to maintain, or reduce if necessary, the temperature of the crude ethanol product to these temperatures. In one embodiment, the crude ethanol product is cooled within these temperatures and held in one or more holding tanks within the above-provided residence times.

In some embodiments, the temperature of the crude ethanol product is related to the residence time of the crude ethanol product, as measured from point A to point B or from point C to point B. For example, maintaining the crude ethanol product at cooler temperatures, may allow longer residence times without additional formation of ethyl acetate. Conversely, when the crude ethanol product is not cooled or is maintained at higher temperatures, additional ethyl acetate may form more quickly. Thus, to avoid additional ethyl acetate formation, residence times preferably would be shorter.

In addition, the rate at which the non-catalyzed reaction occurs may increase as the temperature of the crude product is increased. For example, as the temperature of the crude product in line 115 increases from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C.

Since the crude ethanol product typically is rich in ethanol and contains residual acetic acid, the ethyl acetate concentration in crude ethanol products may tend to increase until the residual acetic acid is removed. In preferred embodiments of the invention, the ethyl acetate in the crude ethanol product prior to acid removal increases by no more than 5 wt. % over the ethyl acetate content in the crude ethanol product withdrawn from the reactor, e.g., no more than 3 wt. % or no more than 2 wt. %. For example, when the crude ethanol product exiting the reactor 103 comprises 5 wt. % of ethyl acetate, the amount of crude ethanol product that is fed to the acid removal unit (first column 107) preferably comprises no more than 10 wt. % of ethyl acetate. Preferably, substantially no additional ethyl acetate is formed between the reactor and acid removal unit.

Embodiments of the present invention beneficially may be used in industrial applications to recover ethanol on an economically feasible scale.

Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication Nos. 2010/0029995, and 2010/0197485, the disclosures of which are hereby incorporated by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 to 99.9 wt. %, e.g., from 78 to 97 wt. %, or from 80 to 95 wt. %. In preferred embodiments that use a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, zinc, and mixtures thereof. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication Nos. 2010/0029995, and 2010/0197485, referred to above, the disclosures of which are incorporated herein by reference.

Embodiments of the invention may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor faun, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is hereby incorporated by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosures of which are hereby incorporated by reference. Optionally, the production of ethanol may be integrated with such methanol carbonylation processes.

U.S. Pat. No. RE 35,377, which is hereby incorporated by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. The disclosures of U.S. Pat. No. 5,821,111, which discloses a process for converting waste biomass through gasification into synthesis gas, and U.S. Pat. No. 6,685,754, are hereby incorporated by reference.

In one optional embodiment, the acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the present of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the disclosure of which is hereby incorporated by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour or at least 600 grams of ethanol per kilogram catalyst per hour, is preferred. In teens of ranges, the productivity preferably is from 200 to 3,000 grams of ethanol per kilogram catalyst per hour, e.g., from 400 to 2,500 or from 600 to 2,000.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 to 70 wt. %, e.g., from 10 to 60 wt. %, or from 15 to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %. Ethyl acetate may also be produced during the hydrogenation of acetic acid or through side reactions and may be present, for example, in amounts ranging from 0 to 20 wt. %, e.g., from 0 to 15 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, acetals, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

FIG. 1 shows a hydrogenation system 100 suitable for the hydrogenation of acetic acid and separating ethanol from the crude ethanol product according to one embodiment of the invention. System 100 comprises reaction zone 101, purification zone 102, and holding tank 130 disposed between reaction zone 101 and purification zone 102. Reaction zone 101 comprises reactor 103, hydrogen feed line 104 and acetic acid feed line 105. Purification zone 102 comprises flasher 106, first column 107, second column 108, and third column 109. Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1, and may be recycled thereto. In addition, although FIG. 1 shows line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 preferably operates at a temperature from 50° C. to 500° C., e.g., from 70° C. to 400° C. or from 100° C. to 350° C. The pressure of flasher 106 preferably is from 50 KPa to 2000 KPa, e.g., from 75 KPa to 1500 KPa or from 100 to 1000 KPa. In one preferred embodiment the temperature and pressure of the flasher is similar to the temperature and pressure of the reactor 103.

The vapor stream exiting the flasher 106 may comprise hydrogen and hydrocarbons, which may be purged and/or returned to reaction zone 101 via line 113. As shown in FIG. 1, the returned portion of the vapor stream passes through compressor 114 and is combined with the hydrogen feed and co-fed to vaporizer 110.

In one embodiment, the liquid from flasher 106 is withdrawn and pumped as a feed composition via line 115 to the purification zone, which comprises first column 107, also referred to as the acid removal unit. Line 115 may, for example, be fed to the side of first column 107. The contents of line 115 typically will be substantially similar to the product obtained directly from the reactor, and may, in fact, also be characterized as a crude ethanol product.

As indicated above, holding tank 130 is disposed between reaction zone 101 and purification zone 102. A portion or all of the liquid feed in line 115 may be fed to holding tank 130 via line 131 and returned to line 115 via line 132. The portion of the liquid feed stored in holding tank 130 may be fed to acid removal unit 107 via line 132 directly or co-fed with the remaining portion of the liquid feed in line 115.

Optionally a portion of the crude ethanol product in line 112 may also be fed to separate holding tank (not shown).

Although one holding tank is shown in FIG. 1, it is contemplated that additional separate tanks may be used. For example, separate holding tanks may be used when both the crude ethanol product in line 112 and liquid feed in line 115 are to be separately stored.

In addition to the holding tank 130, the temperature of the crude ethanol product in line 112 and/or liquid feed in line 115 may be maintained or cooled prior to introduction into the acid removal unit. The crude ethanol product may be maintained or cooled directly in the lines 112 or 115 or the holding tank 130 may be maintained or cooled to a temperature, for example, of less than 40° C., e.g., less than 30° C. or less than 20° C., or in terms of ranges from 0° C. to 40° C., e.g., from 0° C. to 30° C. or from 0° C. to 20° C. If the temperature of lines 112 and/or 115 exceeds these temperatures, the contents of the lines 112 and/or 115 may be cooled as necessary. One or more sensors or monitoring gauges may be used in conjunction with the cooling device for maintaining the temperature.

In one embodiment, the contents of line 115 are substantially similar to the crude ethanol product obtained from the reactor provided that the content of ethyl acetate in the feed to the acid removal unit 107 does not increase by more than 5 wt. % over the content of ethyl acetate in the crude ethanol product withdrawn from the reactor, e.g., more than 3 wt. % or more than 2 wt. %. In addition, the liquid feed may be different than the crude ethanol product because the composition preferably has substantially no hydrogen, carbon dioxide, methane or ethane, which ideally are removed by the flasher 106. Exemplary compositions in line 115 are provided in Table 2. It should be understood that line 115 may contain other components, not listed, such as components in the feed.

TABLE 2

FEED COMPOSITION

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. The feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 115 is less than 5 wt. %, the acid separation column 107 may be skipped and line 115 may be introduced directly to second column 108, also referred to herein as a light ends column.

In the embodiment shown in FIG. 1, line 115 is introduced in the lower part of acid removal unit (first column) 107, e.g., lower half or lower third. In acid removal unit 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. Acid removal unit (first column) 107 also forms an overhead distillate, which is withdrawn in line 117, and which may be condensed and refluxed, for example, at a ratio from 10:1 to 1:10, e.g., from 3:1 to 1:3 or from 1:2 to 2:1.

Any of columns 107, 108 or 109 may comprise any purification column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the purification columns may be of any conventional design and are simplified in FIG. 1. As shown in FIG. 1, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIG. 1, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating purification column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

In addition, it has now been discovered that the above-described equilibrium reaction may also favor ethanol formation in the top region of first column 107.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes.

The first distillate in line 117 is introduced to the second column 108, also referred to as the "light ends column," preferably in the middle part of column 108, e.g., middle half or middle third. In one embodiment, the second column 108 may be an extractive purification column. An extraction agent, such as water, may be added to second column 108. Water, used as an extraction agent, may be obtained from an external source or from an internal return/recycle line from one or more of the other columns.

Second column 108 may be a tray or packed column. In one embodiment, second column 108 is a tray column having from 5 to 70 trays, e.g., from 15 to 50 trays or from 20 to 45 trays.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary distillate and residue compositions for second column 108 are provided in Table 4 below. It should also be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

Without being bound to theory, maintaining or preventing the increase of ethyl acetate in the crude ethanol product prior to introduction into the acid removal unit 107 may improve the efficiency of second column 108 due to the lower content of ethyl acetate.

As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIG. 1, for example, at a reflux ratio from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary distillate and residue compositions for third column 109 are provided in Table 5 below. It should also be understood that the distillate and residue may also contain other components, not listed, such as components in the feed.

TABLE 5

THIRD COLUMN

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the purification process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, purification columns (e.g., a finishing column) or molecular sieves.

Returning to second column 108, the distillate in line 120 preferably is refluxed as shown in FIG. 1, for example, at a reflux ratio from 1:10 to 10:1, e.g., from 1:5 to 5:1 or from 1:3 to 3:1. The distillate from second column 108 may be purged. Alternatively, since it contains ethyl acetate, all or a portion of the distillate from second column 108 may be recycled to reaction zone 101 via line 120 in order to convert the ethyl acetate to additional ethanol. All or a portion the distillate may be recycled to reactor 103, as shown by line 120, and may be co-fed with the acetic acid feed line 105. In another embodiments, the second distillate in line 120 may be further purified to remove impurities, such as acetaldehyde, using one or more additional columns (not shown).

Finished Ethanol

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in copending U.S. Pub. Nos. 2010/0030002 and 2010/0030001, the disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the disclosures of which are hereby incorporated by reference.

In order that the invention disclosed herein may be more efficiently understood, an example is provided below.

EXAMPLES

Example 1

Figure 2:
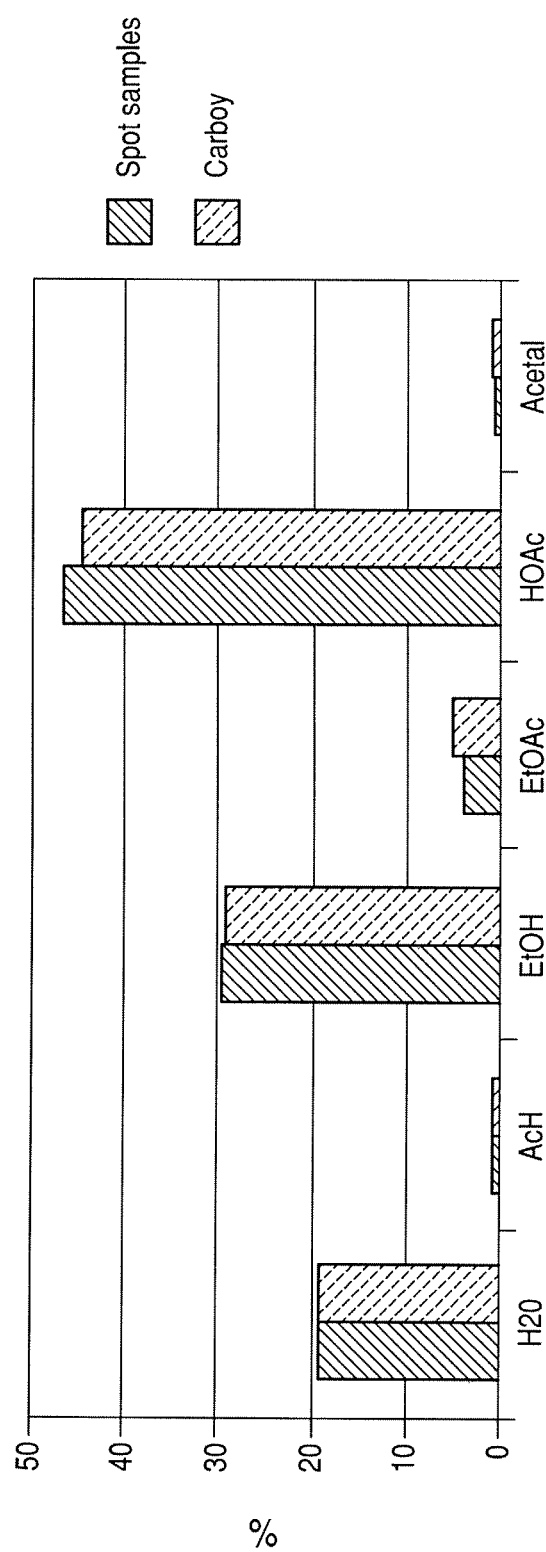
FIG. 2 is a graph indicating the increase in ethyl acetate content.

A crude ethanol product was obtained by hydrogenating acetic acid with a platinum/tin catalyst. The reaction conditions are 3.66 g/min of acetic acid with 10.53 L/min of a recycle flow comprising acetic acid, and 1.05 L/min of hydrogen feed to a reactor having a temperature profile of 220 to 300° C. The residence time from the reactor to the first purification column was 2 days with no temperature control. A spot sample was taken of the crude ethanol product withdrawn from the reactor and the composition was determined by GC. A second sample, i.e., a carboy sample of the liquid feed fed to the purification column, was also taken and the composition was determined by GC. The spot sample and second sample were compared and the results are shown in FIG. 2. An increase of 1.2 wt. % in the content of ethyl acetate was reported between the samples.

Example 2

Figure 3:
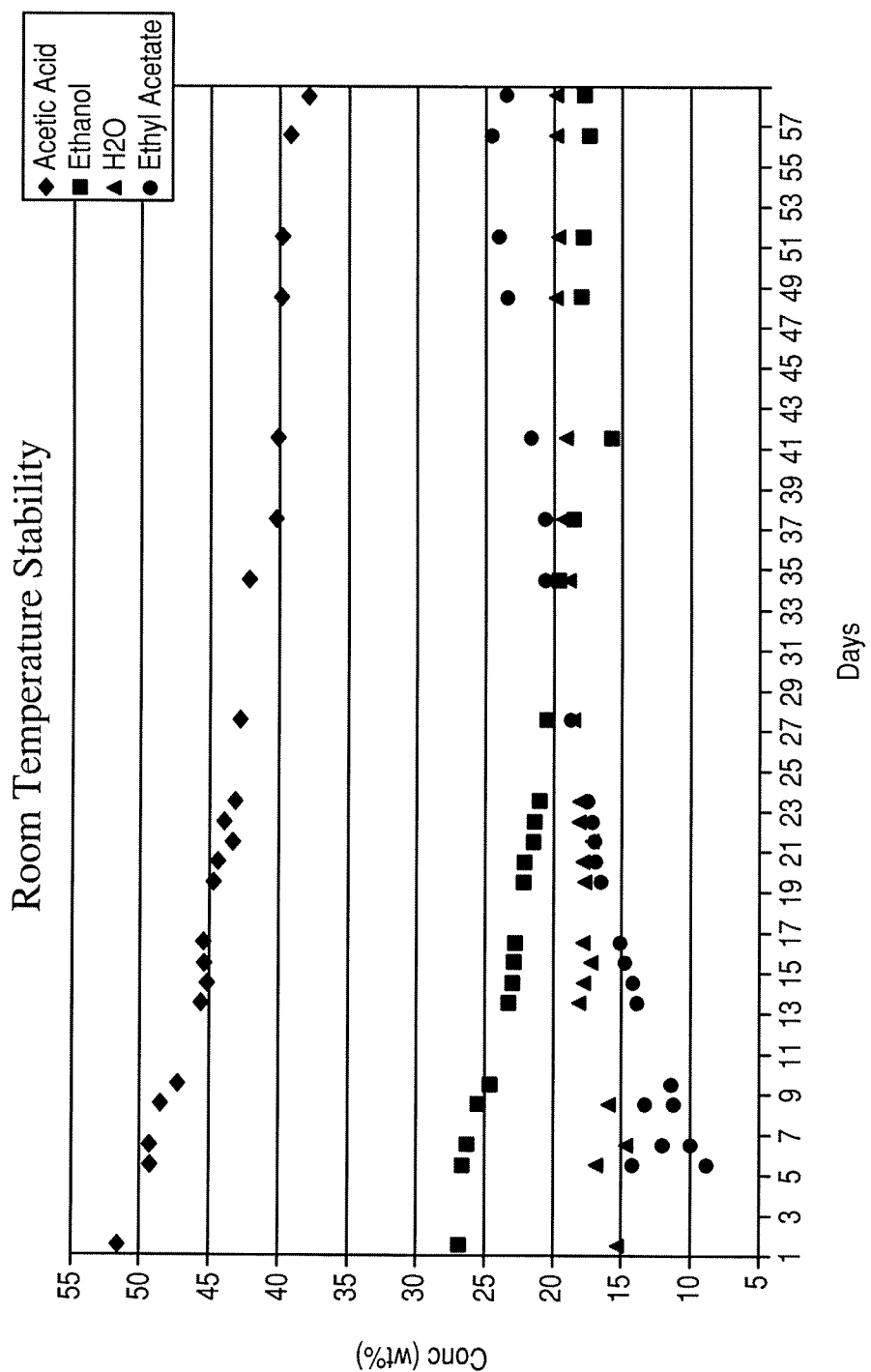
FIG. 3 is a graph of room temperature stability of a crude ethanol product.

A crude ethanol product was obtained by hydrogenating acetic acid with a platinum/tin catalyst. The stability of the crude ethanol product was measured over 57 days. Over this period the amount of ethyl acetate increased and the amounts of ethanol and acetic acid decreased as shown in FIG. 3.

Example 3

A crude ethanol product was obtained by hydrogenating acetic acid with a platinum/tin catalyst. The stability of the crude ethanol product was measured over 27 days at 4° C.

Figure 4:
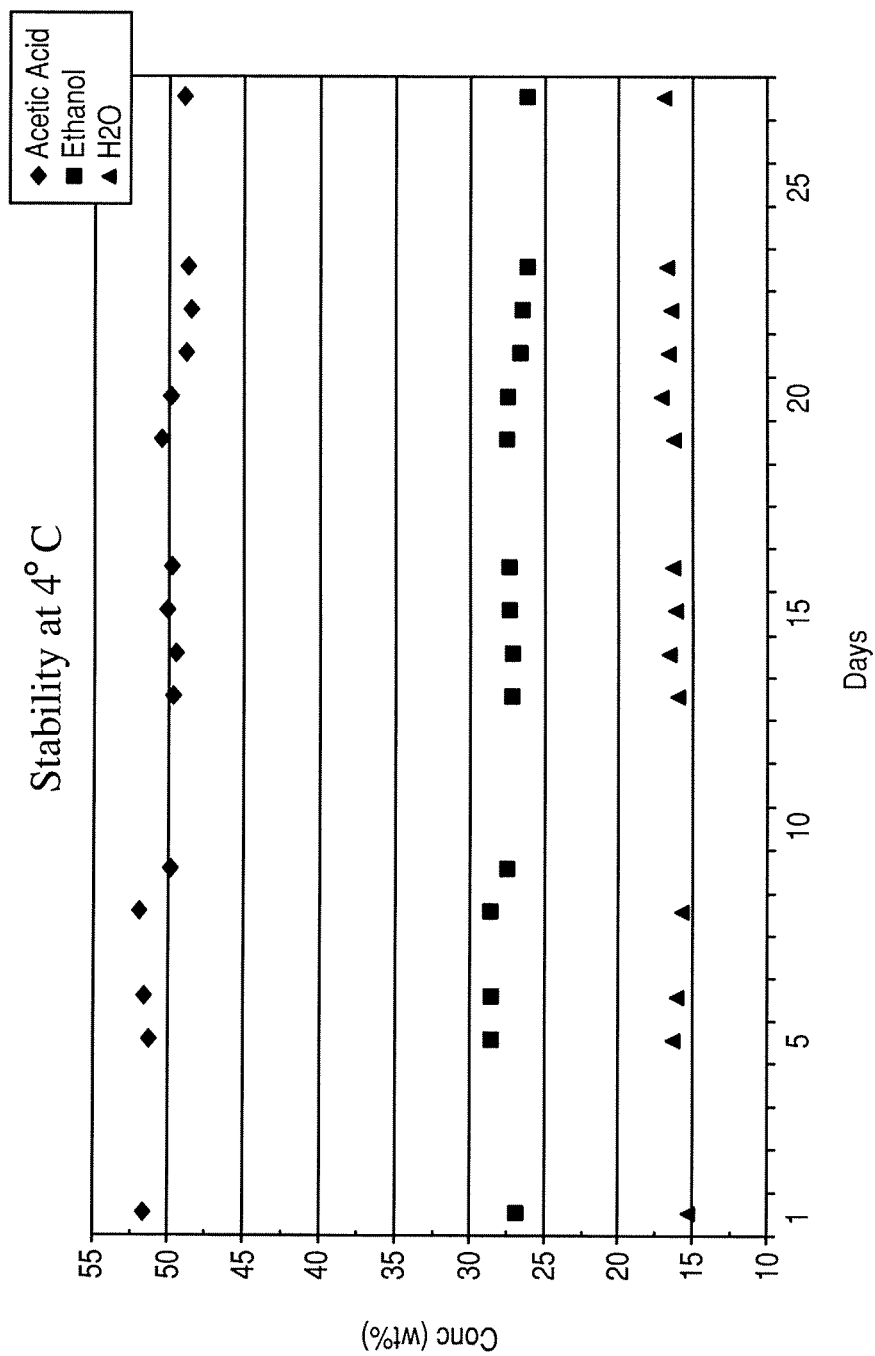
FIG. 4 is a graph of a crude ethanol product stability at 4° C.

Over this period the amounts of ethanol, water, and acetic acid were measured and are shown in FIG. 4.

Example 4

Figure 5:
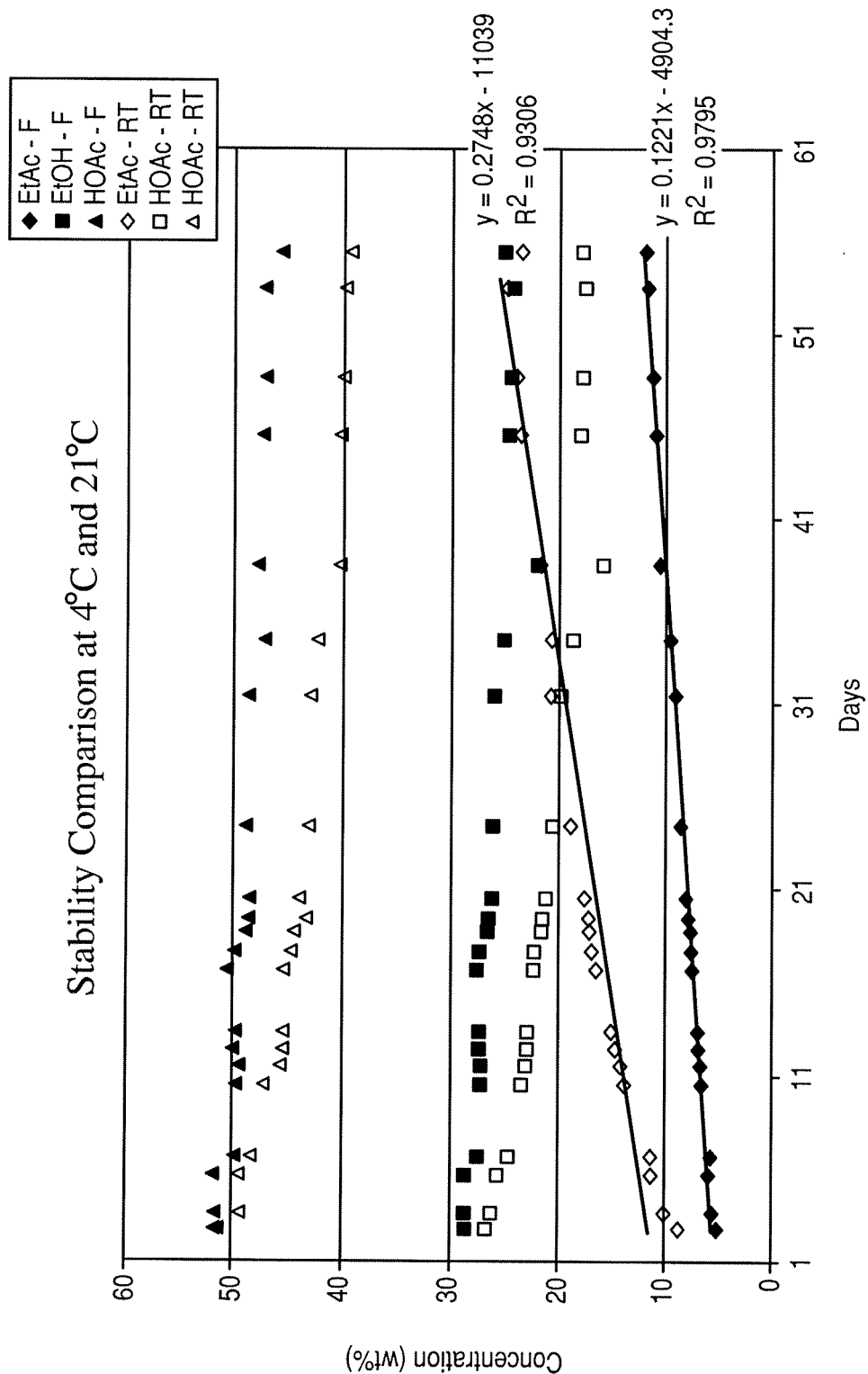
FIG. 5 is a graph a crude ethanol product stability comparison at 4° C. and 21° C.

A crude ethanol product was obtained by hydrogenating acetic acid with a platinum/tin catalyst. The stability of the crude ethanol product was measured over 61 days at 4° C. stored in a refrigerator (F) and compared with the stability of the crude ethanol product stored at room temperature (RT), e.g., 21° C. Over this period the amounts of ethanol, ethyl acetate, and acetic acid were measured and are shown in FIG. 5. The increase in ethyl acetate formation in the top line (RT) was greater than the increase in ethyl acetate formation in the bottom line (F).

Example 5

Figure 6:
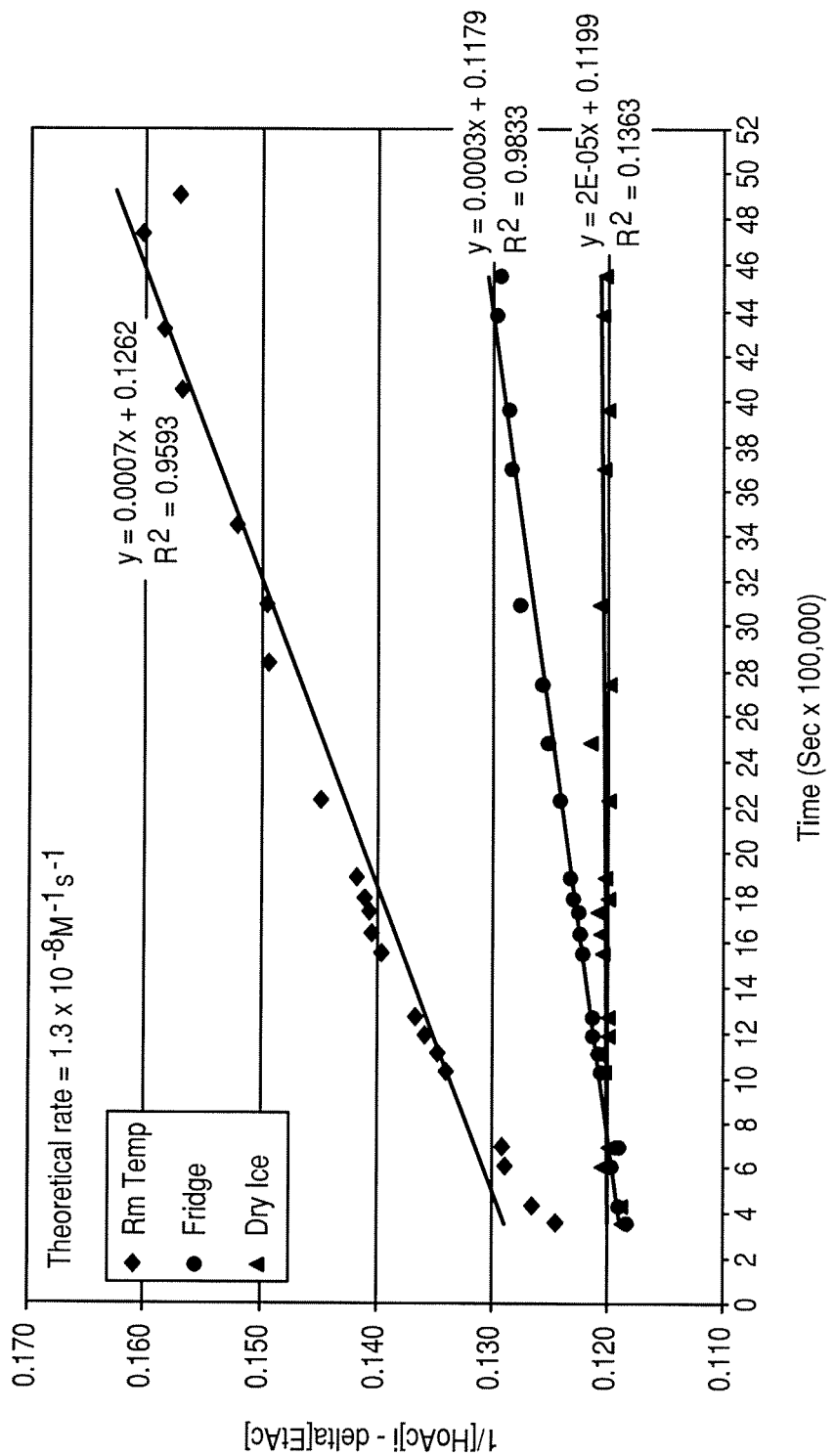
FIG. 6 is a graph a ethyl acetate concentration comparison at −78° C., 4° C., and 21° C.

A crude ethanol product was obtained by hydrogenating acetic acid with a platinum/tin catalyst. The stability of the crude ethanol product stored at three different temperatures was analyzed. The crude ethanol product was analyzed at room temperature (RT), e.g., 21° C.; in a refrigerator (F) at 4° C.; and under dry ice (DI) at −78° C. Over this period the amounts of ethyl acetate were measured and are presented in FIG. 6. The increase in ethyl acetate formation of the crude ethanol composition that was stored under room temperature (RT) was greater than the increase in ethyl acetate formation of the crude ethanol composition that was stored in the refrigerator (F), which was greater than the ethyl acetate formation of the crude ethanol composition that was stored on dry ice (DI).

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are hereby incorporated by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for purifying a crude ethanol product, comprising:
   hydrogenating acetic acid in a reactor in the presence of a catalyst to form the crude ethanol product; and
   separating the crude ethanol product in a flasher into a vapor stream and a liquid stream,
   cooling at least a portion of the liquid stream to a temperature from 0° C. to 40° C.;
   directing at least a portion of the liquid stream to a purification zone; and
   separating at least a portion of the liquid stream in the purification zone into at least one derivative stream.

2. The process of claim 1, wherein the purification zone comprises a first column.

3. The process of claim 1, wherein the separating comprises separating at least a portion of the crude ethanol product in the first column into a first distillate comprising ethanol, water, and ethyl acetate and a first residue comprising acetic acid.

4. The process of claim 3, further comprising returning at least a portion of the first residue to the reactor.

5. The process of claim 3, wherein the first residue comprises from 60 to 100 wt. % of acetic acid, based on the total weight of the first residue.

6. The process of claim 1, further comprising the step of returning at least a portion of the vapor stream to the reactor.

7. The process of claim 1, wherein ethyl acetate content of the crude ethanol product increases by no more than 5 wt. % prior to being introduced into the purification zone.

8. The process of claim 1, wherein at least a portion of the crude ethanol product stream is directed to a holding tank.

9. The process of claim 1, wherein the crude ethanol product comprises ethanol, water ethyl acetate, and acetic acid.

* * * * *